US006224914B1

(12) United States Patent
Han et al.

(10) Patent No.: US 6,224,914 B1
(45) Date of Patent: May 1, 2001

(54) PROCESS FOR INCORPORATING WHEY PROTEINS INTO CHEESE USING TRANSGLUTAMINASE

(75) Inventors: Xiao-Qing Han, Glenview, IL (US); Joseph E. Spradlin, Hot Springs, AR (US)

(73) Assignee: Kraft Foods, Inc., Norhtfield, IL (US)

( * ) Notice: Subject to any disclaimer, the term of this patent is extended or adjusted under 35 U.S.C. 154(b) by 0 days.

(21) Appl. No.: 09/325,217

(22) Filed: Jun. 3, 1999

(51) Int. Cl.$^7$ ....................................................... A23C 9/12
(52) U.S. Cl. ................................. 426/36; 426/34; 426/40; 426/42; 426/582
(58) Field of Search ................................. 424/34, 36, 40, 424/41, 42, 580, 582

(56) References Cited

U.S. PATENT DOCUMENTS

| 3,535,304 | 10/1970 | Muller et al. . |
| 4,205,090 | 5/1980 | Maubois et al. . |
| 5,156,956 | 10/1992 | Motoki et al. . |
| 5,356,639 | 10/1994 | Jameson et al. . |
| 5,523,237 | 6/1996 | Budtz et al. . |
| 5,681,598 | 10/1997 | Kuraishi et al. . |
| 5,731,183 | 3/1998 | Kobayashi et al. . |

FOREIGN PATENT DOCUMENTS

| 59-059151 | 4/1984 | (JP) . |
| 02276541 | 11/1990 | (JP) . |
| 93/22930 | 11/1993 | (WO) . |
| 94/21129 | 9/1994 | (WO) . |
| 94/21130 | 9/1994 | (WO) . |
| 97/01961 | 1/1997 | (WO) . |

OTHER PUBLICATIONS

Ernstrom et al., J. Dairy Science 63:228–234 (1980).
Banks, J.M. et al., IG [1987]. Increasing the yield of Cheddar Cheese by the acidification of milk containing heat–denatured whey protein. Milchwissenschaft 42 (4), pp. 212–215.
Law, A.J.R. et al., IG [1994]. Denaturation of the whey proteins in heat milk and their incorporation into Cheddar cheese. Milchwissenschaft 49 (2), pp. 63–67.
Guinee, Timothy P. et al., Composition, Microstructure and Maturation of Semi–Hard Cheeses From High Protein Ultra-filtered Milk Retentates With Different Levels of Denatured Whey Protein, Int. Dairy Journal 5, p. 543–568, 1995.
Han, Xiao–Qing et al., [1996]. Thermodynamic Compatibility of Substrate Proteins Affects Their Cross–Linking by Transglutaminase. J. Agri. Food Chem. 44 (5) pp. 1211–1217.
Dybing S. T., et al. [1998], Dairy Foods—The Ability of Phosphates or —Carrageenan to Coagulate Whey Proteins and the Possible Uses of Such Coagula in Cheese Manufacture. J. Dairy Sci. 81 (2) pp. 309–317.
Dalgleish, D. G., et al., [1997] Heat–Induced Interactions of Whey Proteins and Casein Micelles with Different Concentrations of α–Lactalbumin and β–Lactoglobulin, J. Agric. Food Chem., 45, pp. 4806–4813.
Dalgleish, D. G., et al. [1997] Interactions between α–Lactalbumin and β–Lactoglobulin in the Early Stages of Heat Denaturation, J. Agric Food Chem. 45 pp. 3459–3464.
Noh, B., et al. [1989] Incorporation of Radiolabeled Whey Proteins into Casein Micelles by Heat Processing, J. Dairy Sci. 72 pp. 1724–1731.
Noh, B., et al. [1989] Radiolabelling Study of Heat–induced Interactions Between α–Lactalbumin, β–Lactoglobulin and K–Casein in Milk and in Butter Solutions, Journal of Food Science, vol. 54, No. 4, pp. 889–893.
Kosikowski, Cheese and Fermented Foods, 2$^{nd}$ ed. Edward Brothers, Inc., Ann Arbor, MI, 1977, pp. 451–458.

*Primary Examiner*—Leslie Wong
(74) *Attorney, Agent, or Firm*—Fitch, Even, Tabin & Flannery

(57) ABSTRACT

The present invention provides a cheese curd containing a substantial proportion of whey protein products and curded proteins originating from a dairy liquid containing casein, as well as a process for making the cheese curd. The process includes the significant step that a dairy liquid fortified with whey protein is contacted with a transglutaminase to provide a modified dairy liquid containing whey protein products. The modified dairy liquid is then blended with a second dairy liquid and renneted to provide the curd, whereby a high proportion of whey protein products is retained in the curd. The curd can be used to prepare cheese products, including soft, semi-soft, and hard cheeses, where the cheese products contain a substantial proportion of whey protein products and curded proteins originating from dairy liquids.

12 Claims, 2 Drawing Sheets

PROCESS FOR INCORPORATING WHEY PROTEINS INTO CHEESE USING TRANSGLUTAMINASE

FIELD OF THE INVENTION

This invention relates to a method that allows the incorporation of large amounts of whey protein into cheese. The method involves the action of a transglutaminase on the whey protein to prepare cheese curd incorporating a significant proportion of whey protein.

BACKGROUND OF THE INVENTION

Cheese compositions are generally prepared from dairy liquids by processes that include treating the liquid with a coagulating or clotting agent. The coagulating agent may be a curding enzyme, an acid, or a suitable bacterial culture or it may include such a culture. The coagulum or curd that results generally incorporates transformed casein, fats including natural butter fat, and flavorings that arise especially when a bacterial culture is used. The curd is usually separated from the liquid whey, which generally contains soluble proteins not affected by the coagulation; such proteins are, of course, not incorporated into the coagulum. The inability of whey proteins to be retained in the coagulum is an important factor contributing to a lack of efficiency in production of cheese curds, and to a reduction in overall yield. Failure to incorporate a significant amount of the protein solids that are present in the starting dairy liquids into the resulting cheese curds represents a significant loss of protein. These problems have been recognized for many years.

Several methods have been proposed early with the objective of recovering whey proteins in cheese products. For example, whey proteins have been concentrated or dried from whey, and then recombined with cheese (see, e.g., Kosikowski, Cheese and Fermented Foods, 2nd ed., Edwards Brothers, Inc., Ann Arbor, Mich., 1977, pp. 451–458). Unfortunately the cheese recovered from such procedures does not have the appropriate physical and chemical properties conducive to making good quality natural cheeses or process cheeses.

An alternative approach has been to coprecipitate whey proteins with casein, as disclosed, for example, in U.S. Pat. No. 3,535,304. Again, however, the final product of this process lacks the proper attributes for making processed and imitation cheeses.

A further attempt to incorporate whey proteins into cheese products used ultrafiltration of milk to concentrate all the components, such as the casein, the whey protein, and the butterfat, that do not permeate the ultrafiltration membrane. When such a composition is coagulated by contact with an acid or rennet, a curd forms. This curd, however, loses considerable quantities of the whey protein during compaction. An example of such a process is provided in U.S. Pat. No. 4,205,090 wherein the milk is concentrated to about one-fifth of its original volume. The resulting curd could only be used to provide soft cheeses such as Camembert or Roblechon. Hard cheeses, such as cheddar, Colby, and the like, could not be prepared using this product.

Ernstrom et al. (J. Dairy Science 63:2298–234 (1980)) described a process in which milk is concentrated to about 20% of the original volume by ultrafiltration, diafiltration, and evaporation. The resulting composition is then inoculated with a cheese starter to ferment the lactose and form a cheese base. The cheese base can be used to replace natural cheese components of process cheese. This process does not employ any renneting step to prepare a cheese curd.

Food processing methods employing transglutaminases have also been disclosed in recent years. For example, Japanese Patent 59059151 discloses treating an emulsion containing proteins, oils or fats, and water with transglutaminase to produce a gelatinous, crosslinked gel. Japanese Patent 02276541 discloses a food protein with a fiber texture having heat-resistance. The fiber texture is developed by treatment of a protein hydrogel with a transglutaminase in the presence of calcium ion to induce crosslinking of the surface of a fiber bundle. Japanese Patent 2131539 used transglutaminase to work on a fused cheese product containing milk solids to product a cheese food having a texture similar to boiled fish paste.

U.S. Pat. No. 5,156,956 discloses a transglutaminase purified from strains of the genus Streptoverticillium, as well as its chemical, physical, and enzymatic properties. This transglutaminase catalyzes formation of protein gelation products from protein solutions to produce conventional gel foodstuffs such as yoghurt, jelly, cheese, gel cosmetics, and the like. This method did not use transglutaminase and enzymatic clotting agents to produce cheese.

U.S. Pat. No. 5,356,639 discloses a process for the production of a fermented concentrate from milk, including whole milk, skim milk, and milk with added milk components. The concentrate could be used to make cheese. The process includes the steps of (1) selectively concentrating milk; (2) increasing the ionic strength of the concentrate to maintain the milk in the liquid phase (coagulum formation is prevented both during and after fermentation); (3) fermenting the concentrate with lactic acid producing bacteria; and (4) removing water from the fermented liquid concentrate. The final product includes substantially all of the whey proteins originally present in the milk.

U.S. Pat. No. 5,681,598 describes a process for producing cheese with a transglutaminase. The process includes (1) adding a transglutaminase to a milk or milk protein solution, (2) heat-treating the mixture, (3) adding a milk clotting enzyme for a fixed time, and (4) recovering a cheese. This process provides a large amount of cheese curd compared to conventional methods. Additionally, processes in which conventional cheese fermentation occurs first and transglutaminase treatment occurs subsequently, as well as simultaneous treatments, are disclosed. The milk clotting enzyme is preferably an animal rennet. Increases in total weight, but not in dry weight, of the curd when transglutaminase is used were observed.

U.S. Pat. No. 5,731,183 discloses a transglutaminase purified from strains of Bacillus subtilis, having particular physical and enzymatic characteristics, and a method for producing protein, peptide, or non-protein amino acid polymers that are cross-linked via their glutamine and lysine residues to form intermolecular or intramolecular conjugates. The transglutaminase may be used to produce crosslinked protein polymers that can be used in a variety of food substances including cheese. This reference differs from the instant disclosure in characterizing a bacterial transglutaminase while not disclosing process steps utilizing transglutaminase and clotting agents that are involved in producing cheese.

Banks et al. (*Milchwissenschaft* 42:212–215 (1987)) disclose that heating milk at temperatures from 95° C. to 140° C. and then acidifying permits a modest increase in protein content in the cheese upon Cheddar production. Unfortunately, the resulting cheese developed a bitter off-flavor in this process. Law et al. (*Milchwissenschaft* 49:63–37 (1994)) report that heat treatment of milk prior to cheddaring results in reduction of proteins in whey and/or in acid filtrates of the milk.

Han et al. (*J. Agn. Food Chem.* 44:1211–1217 (1996)) examined the activity of transglutaminase in forming heterologous dimers and trimers. It was found that β-casein forms homopolymers whereas β-lactoglobulin does not. In heterologous mixtures, transglutaminase was shown to catalyze dimer formation between α-lactalbumin and β-casein but not between β-casein and β-lactoglobulin. Han et al. do not discuss any aspect of cheese production.

U.S. Pat. No. 5,523,237 discloses a plastein material which is defined as one made by reversing the activity of a protease enzyme (e.g., a serine protease) acting on proteinaceous material. The proteinaceous substrate is present at a concentration of 5–50%, and is preferably whey, casein, or soy protein. The enzyme preparation is substantially free of subtilisin A activity, and is specific for glutamic acid and aspartic acid residues. This protease is obtained from *Bacillus licheniformis* and is designated SP 446; its proteolytic activity is characterized in considerable detail. The viscosity of whey protein containing solutions is shown to increase as a result of the action of the enzyme.

International patent WO 93/22930 discloses treating milk with a transglutaminase (preferably mammalian activated Factor XIII) and then with an enzyme having milk clotting activity to provide a milk-like product. According to this publication, the product has microparticulated protein that has been aggregated by means of the enzyme with milk clotting activity, and has mouthfeel that resembles a fat emulsion. Preferably the milk clotting enzyme is a cheese rennet enzyme. This method, like that of U.S. Pat. No. 5,356,639, does not appear to provide a cheese curd.

International patent WO 94/21129 discloses a process for forming an acidified edible gel from milk. Transglutaminase is added to milk or a milk-like product, the pH is adjusted to 4.8 to 5.8, and the resulting composition is exposed to a heat treatment. The resulting edible gel is reported to have a pleasant consistency and mouthfeel.

International patent WO 94/21130 discloses a similar process for forming an edible gel from milk. Transglutaminase is added to milk or a milk-like product, rennet is then added, and the resulting composition is exposed to a heat treatment. Only a single phase gel (rather than separate curd and whey) was obtained. This gel is reported to have satisfactory organoleptic properties.

International patent WO 97101961 discloses a process for making cheese which retains proteins in the cheese. The milk is incubated with transglutaminase, followed by a treatment with a rennet to cause clotting and formation of a coagulate. After separating the whey from the coagulate, the coagulate is used to make cheese. The protein to be maintained in the cheese, as set forth in the description, relates to casein macropeptides that result from the action of the rennet, and that diffuse into the whey. This process differs from the instantly claimed invention in a number of ways. The process disclosed in this patent relates to the retention of casein macropeptides, rather than whey protein, in the cheese curd. Moreover, there is no requirement for an initial heating step, and the rennet employed in WO 97101961 is a conventional mammalian rennet.

Dybing et al. (*J. Dairy Sci.* 81:309–317 (1998)) postulated incorporating whey protein into cheese curd by concentrating the components, coagulating whey proteins using a variety of agents, and renneting a composition containing the coagulated whey protein and concentrated milk components. It was found, however, that none of the methods attempted succeeded in producing whey protein coagula that were recovered as cheese.

Guinee et al. (*Int. Dairy Journal* 5:543–568 (1995)) reviewed the state of the art relating to incorporation of whey protein into cheese. High-heat treatment of milk impairs rennet coagulation, curd syneresis, curd structure and texture, as well as functional properties such as meltability and stretchability. Guinee et al. discuss physical and chemical factors that may be responsible for these effects. In heat treatments that denature whey protein in milk compositions, they found that, in semi-hard cheeses that result from curding such treated compositions, the curd has higher whey protein levels, but also higher moisture level, lower pH value, poorer curd fusion, and lower yield (fracture) values during ripening.

In spite of many attempts documented over almost three decades of effort, there remains a need for a cheese curd with a significant incorporation of whey protein into the curd without significant reduction of organoleptic properties and for a method that significantly increases the incorporation of whey protein into cheese curd without adversely affecting the organoleptic and other properties of the resulting cheese. There further remains a need for cheese products prepared using excess whey protein that significantly increases retention of the whey protein, and for a method of making cheese products using excess whey protein that significantly increases the incorporation of whey protein into the cheeses. Additionally there remains a need for enhancing the yield and efficiency of making cheese with increased incorporation of whey protein into cheese products. The present invention addresses these long-felt needs.

SUMMARY OF THE INVENTION

The present invention provides, in a first aspect, a cheese curd containing a substantial proportion of whey protein products and curded proteins originating from a dairy liquid comprising casein, as well as a process for making the cheese curd. The process includes the sequential steps of:

(i) providing a first dairy liquid fortified with whey protein;

(ii) contacting the fortified dairy liquid with a transglutaminase to provide a modified dairy liquid containing whey protein products;

(iii) blending the modified dairy liquid with a second dairy liquid containing casein to provide a dairy mixture;

(iv) contacting the dairy mixture with a rennet to form cheese curd and whey liquid; and (v) obtaining the cheese curd by separating it from the whey liquid; whereby a high proportion of whey protein products is retained in the curd. The resulting curd may be used to prepare natural cheeses and/or process cheeses using conventional techniques and procedures.

In an important embodiment of the cheese curd and the process, the transglutaminase is selected from among transglutaminases isolated from a microbial source, a fungus, a mold, a fish, and a mammal; more importantly, the transglutaminase is isolated from a microbial source, and still more importantly the transglutaminase is isolated from the genus Streptoverticillium.

In a significant embodiment of the cheese curd and the process, the first dairy liquid is optionally heated to a temperature of about 55 to about 90° C. for from about 2 to about 40 minutes and then cooled to a temperature from about 35 to about 60° C. before the addition the transglutaminase. Additionally, in an advantageous embodiment of the cheese curd and the process, the modified dairy liquid is optionally heated at a temperature from about 80 to about 95° C. for about 5 to about 20 minutes and then cooled; the resulting modified dairy liquid is then blended with the second dairy liquid. If desired, the second dairy liquid can be cultured prior to being added to the modified dairy liquid. The cheese curd can be used to prepare natural or process cheeses, including soft, semi-soft, and hard cheeses.

DETAILED DESCRIPTION OF THE INVENTION

The present invention provides a cheese curd from dairy liquids containing whey protein and casein. The curd composition contains protein products provided by first subjecting a first dairy liquid fortified with whey protein to the action of a transglutaminase, thereby providing whey protein products, then combining the resulting mixture with a second dairy liquid containing casein, and coagulating the resulting mixture. The resulting cheese curd retains a substantial proportion of the whey protein products. This curd can be further processed to provide cheese products including soft, semi-soft, or hard cheeses. The invention also provides methods for making the cheese curd and the cheese product. The retention of the whey protein products in the cheese curd, and in the cheese products, provides a significant enhancement in the efficiency of utilization of the total protein in the starting raw material (i.e., the dairy liquid), while retaining agreeable organoleptic properties. This result also provides a higher yield of edible, nutritive solids in the products than is found in cheeses currently available. As noted above, U.S. Pat. No. 5,156,956 describes use of transglutaminase to catalyze formation of protein gelation products. The method of the patent does not use transglutaminase and enzymatic clotting agents to produce cheese. In particular, it is shown herein that, in contrast to this patent, treating solutions of whey proteins with transglutaminase yields soluble cross-linked whey protein polymers that can be readily incorporated into cheese curd after the addition of milk. The present method results in the incorporation of substantial quantities of whey protein into cheese curd, which can then be used to produce cheeses having a wide variety of textures and flavors. It is shown herein that the final curd consists of up to about 50 percent (and perhaps more) whey protein products.

Figure 1:
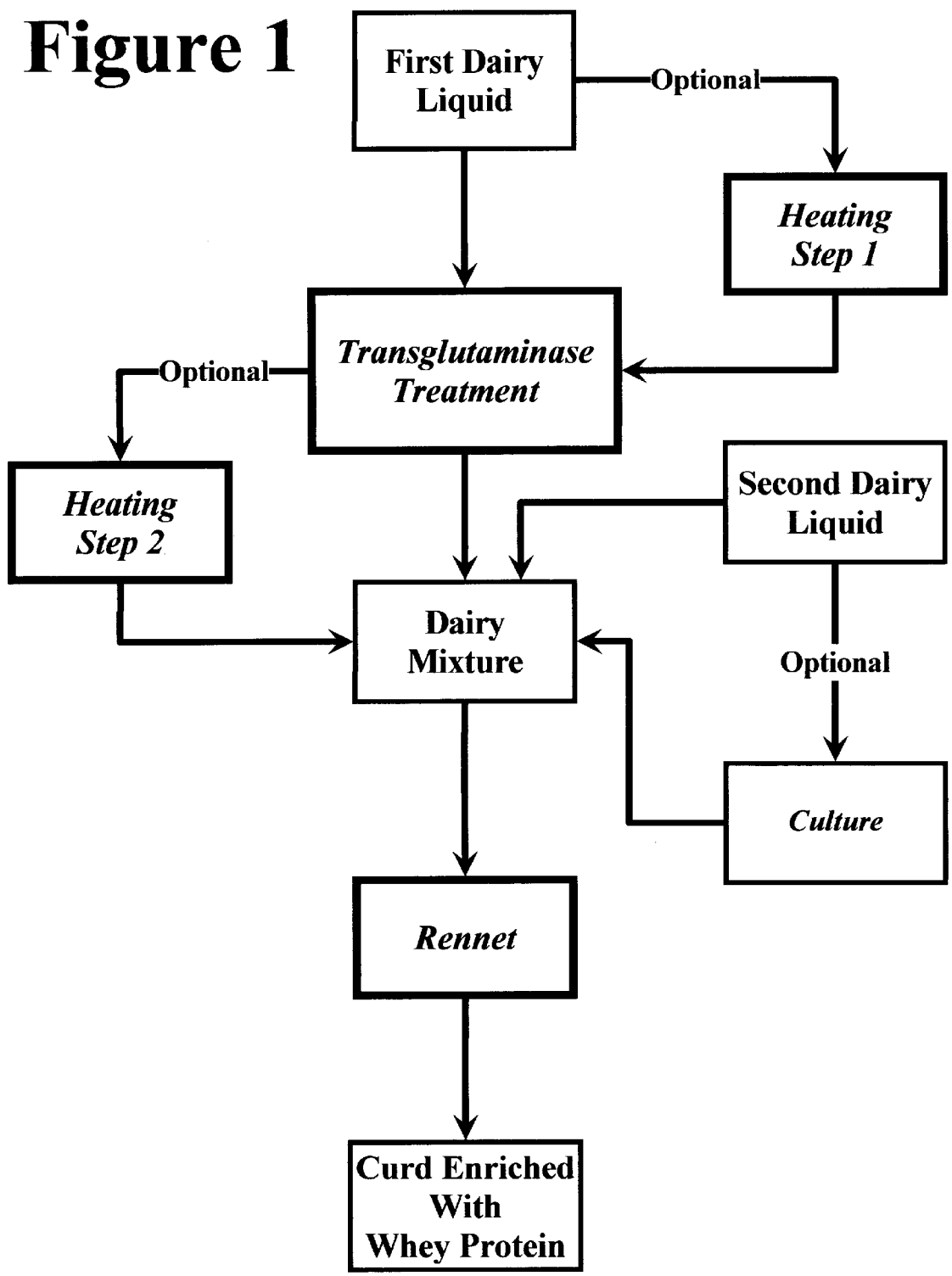
FIG. 1 provides a schematic flow chart of various embodiments of the present invention. Optional process steps are so labeled. Italics and heavy boxes indicate the occurrence of physical, enzymatic, or microbiological transformation steps.

FIG. 1 provides a general schematic flow chart for the process of the invention leading to the production of a curd that retains a substantial proportion of whey protein products therein. Optional steps are indicated and labeled as "optional." Italics and heavier boxes are used to indicate steps in which physical, enzymatic, or microbiological transformations take place (i.e., heating steps 1 and 2, transglutaminase treatment, culturing step, and culturing step).

The starting material of the present invention is a first dairy liquid that preferably includes or is fortified with a high proportion of whey protein, such as whey protein concentrated from the whey arising during a cheese making process. Preferably the second diary liquid (see FIG. 1) contains casein, such as any milk described in the following, but is, in general, not fortified with whey protein. As used generally herein, "dairy liquid" relates to milk, milk products obtained by fractionating raw milk to provide a liquid fraction, or a solid milk fraction that is reconstituted to a liquid. For example, the milk may be treated to remove some or all of the butterfat, providing low fat milk or skim milk, respectively. Furthermore, whole milk, low fat milk, or skim milk may be concentrated by methods such as evaporation and/or ultrafiltration (with or without diafiltration) and the like. Evaporation provides dairy liquids containing a higher concentration of all the nonvolatile components, whereas ultrafiltration provides dairy liquids with a higher concentration of the components that do not permeate the ultrafiltration membrane. In any case, the dairy proteins including casein and whey protein are included among the retained solids, such that their concentrations in the resulting liquids are increased. Furthermore, the above dairy liquids may be evaporated to dryness, providing milk solids originating from whole milk, low fat milk, or skim milk. Any of these solids may be reconstituted by the addition of water or a suitable aqueous composition including milk or a milk fraction. Reconstitution of dry milks thus provides dairy liquids that in general may have a broad range of final concentrations of the component proteins, butterfat, and other components. All the above liquids are included in the designation of "dairy liquids" as used herein.

The dairy liquids employed in the present invention may originate from any lactating livestock animal whose milk is useful as a source of human food. Such livestock animals include, by way of nonlimiting example, cows, buffalo, other ruminants, goats, sheep, and the like. Generally, however, cows' milk is the preferred dairy liquid used in the practice of the invention.

As used herein, "whey protein" relates to the proteins contained in whey, a dairy liquid obtained as a supernatant of the curds when milk or a dairy liquid containing milk components is curded to produce a cheese-making curd as a semisolid. Whey protein is generally understood to include principally the globular proteins β-lactoglobulin and α-lactalbumin. It may also include significantly lower concentrations of immunoglobulin and other globulins. As used herein, the "first dairy liquid" as set forth above may further relate to a liquid containing whey protein, and in particular may relate to a liquid containing a high proportion of whey protein obtained, for example, by concentrating whey using a procedure such as evaporation or ultrafiltration. Such a dairy liquid fortified with whey protein may also be obtained by reconstituting whey protein solids using water or any of the dairy liquids described above.

As used herein, "casein" relates to any, or all, of the phosphoproteins in milk. Important characteristics of casein are that it forms micelles in naturally occurring milk and in the dairy liquids employed in the present invention, and that clotting a dairy liquid containing casein by any suitable means provides a coagulated curd phase and a liquid whey phase that are separable from one another. Many casein components have been identified, including but not limited to, α-casein (including $\alpha_{s1}$-casein or $\alpha_{s2}$-casein), β-casein, κ-casein, their genetic variants, and mixtures thereof. As noted above, preferably the second diary liquid (see FIG. 1) contains casein but is, in general, not fortified with whey protein. This second dairy liquid can, however, contain whey protein; but such whey protein will be retained in the curd to such extent as the retained whey protein from the first dairy liquid.

Transglutaminases are enzymes which catalyze the transfer of the γ-carboxamide group of a glutaminyl residue in a protein or peptide to the ε-amino of a lysyl residue of the same or a different protein or peptide, thereby forming a γ-carboxyl-ε-amino crosslink. Transglutaminases have a broad occurrence in living systems, and may be obtained, for example, from microorganisms such as those belonging to the genus Streptoverticillium, or from *Bacillus subtilis*, from various Actinomycetes and Myxomycetes, from plants, from fish species, and from mammalian sources including the blood clotting protein activated Factor XIII. In general, transglutaminases from animal sources require calcium ions for activity. Recombinant forms of transglutaminase enzymes may be obtained by genetic engineering methods as heterologous proteins produced in bacteria, yeast, and insect or mammalian cell culture systems. The principal requirement of any transglutaminase employed in the instant invention is that it have the cross-linking activity discussed above. Any enzyme having such transglutaminase activity may be employed in the methods of the present invention. In a preferred embodiment, the transglutaminase is obtained from the genus Streptoverticillium.

Transglutaminase activity may be determined using known procedures. One such colorimetric procedure uses benzyloxycarbonyl-L-glutaminyl-glycine and hydroxylamine to form a γ-carboxyl-hydroxamic acid if transglutaminase is present. An iron complex of the hydroxamic acid can be formed in the presence of ferric chloride and trichloroacetic acid. Using the absorbance at 525 nm with appropriate standards, the activity of enzyme present may be determined. See, for example, U.S. Pat. No. 5,681,598.

"Rennet" is a generic term in the fields of dairy science and cheese making and is used to designate an activity obtained from the lining of the stomachs of immature mammals that consume maternal milk. The natural function of rennet is to initiate the digestion of the milk in order to provide the nutrition contained in the milk protein to the young mammal. In cheese making, rennet is used to clot dairy liquids, thereby forming cheese curd and whey. The term "renneting" relates to the process of treating a dairy liquid with a rennet to provide a cheese curd and whey. Synonyms for "renneting" include "curding", "clotting", and "setting". As used in contemporary dairy science, "rennet" connotes the enzyme earlier called "rennin" and now termed "chymosin". Chymosin is a member of the family of proteases known as aspartyl proteases.

The activity of chymosin on dairy liquids includes at least the proteolytic cleavage of the peptide bond between the phenylalanyl residue that occurs at about the position numbered 105 and the methionine that occurs at about the position numbered 106 in κ-casein to release a soluble macropeptide and induce the coagulation of the remainder of the molecule, termed para-κ-casein, with all the components of the casein micelles. Common natural sources of chymosin include, but are not limited to, the stomachs of calves, buffalo, other ruminants, kid goats, lambs, piglets, and the like. Furthermore, various natural chymosins and genetically engineered chymosin mutant proteins are available as the recombinant protein products, obtained as a result of introducing genes encoding these proteins as heterologous genes in order to make the gene products in suitable host organisms. Chymosin is the activated form produced when the proenzyme prochymosin is activated. Prochymosin likewise may be a recombinant product, and may be a genetically engineered mutant protein which upon activation provides renneting activity. As used herein, all such chymosins having renneting activity, and prochymosins activatable to such chymosins, are included in the term "rennet".

Rennets are generally active in a pH range from about 4 to about 8, and in a temperature range from about 20 to about 50° C. In general, the time of digestion may vary from about 5 to about 120 minutes or even longer. It is preferred to specify digestion conditions such that the digestion time is kept to a convenient duration, such as about 30 to about 60 minutes. The duration of treatment under a given set of conditions may be readily determined by a worker of skill in the field of cheese making by optimizing the incorporation of whey protein digestion products into cheese curd using those conditions. The coagulation procedure provided by the present invention unexpectedly yields a cheese curd that retains a significant proportion of the whey protein originally employed as the whey-fortified dairy liquid in the form of a whey protein product.

As noted above, a first important step is provision of a first dairy liquid containing whey proteins. An important objective of the present invention is the use of whey protein obtained as a by-product from prior cheesemaking operations. For this reason, a significant embodiment of the present invention relates to employing a first dairy liquid that is fortified with added whey protein. The added whey protein may be provided from concentrated whey, or from reconstituted whey solids or whey protein solids. In a particularly significant embodiment, the first dairy liquid is a concentrated solution of whey protein. As used herein, the terms "fortified" and a "concentrated solution" when referring to the preferred first dairy liquid containing whey protein is intended to mean a dairy liquid containing at least about 5 percent, preferably at least about 10 percent, and even more preferably at least about 20 percent.

The process of the present invention, including several optional steps, is illustrated in FIG. 1. The first dairy liquid can be acted upon by a transglutaminase without any preliminary treatment. In an alternative embodiment, however, the first dairy liquid may be heated at a temperature between about 55 and about 90° C. (heating step 1 in FIG. 1). Of course, the upper limit of this temperature range is limited in order to avoid detrimental occurrences such as foaming or precipitation of the proteins in the liquid, development of excessive vapor pressure if the heating is done in a closed system, or the like. In preferred embodiments, the temperature of this heating step 1 is between about 65 and about 850° C., and more preferably, between about 75 and about 77° C. Heating step 1, when used, is carried out for a relatively extended period of time which is sufficient to alter the state of the proteins in the dairy liquid in such a way as to permit the transglutaminase to act more effectively. Thus, this heating step is continued for at least 2 minutes and more preferably for about 10 about 40 minutes. Without wishing to be limited by theory, it is believed that this heat treatment effects a partial denaturation or unfolding of the proteins in the dairy liquid; the desired cross linking can be more effectively carried out if the proteins are at least partially denatured or unfolded. For this reason, this heating step is to be distinguished from a transient heating, such as a pasteurization heating, which in general may be carried out at a temperature of about 72 to about 120° C. for only a brief time interval (generally from about 2 to about 90 seconds); such a pasteurization step should not significantly effect the structure of the dairy liquid. When employed in the present invention, this optional heating step affords an important initial step in the present process of making a cheese curd or a cheese product leading to retention of a significant proportion of whey protein products. Following the heating step, the dairy liquid is cooled to a temperature suitable for the introduction of a transglutaminase. Generally, such cooling is to a temperature between about 35 and about 60° C.

The next step in the present invention is the transglutaminase treatment step. The first dairy liquid (either directly or after heating step 1) is contacted with a transglutaminase. Preferably the first dairy liquid is fortified with whey protein. An amount of transglutaminase having sufficient activity to modify the dairy liquid as described herein is required. The known enzymatic function of transglutaminase is to catalyze the transfer of the γ-carboxamide group of a glutaminyl residue in a protein or peptide to the ε-amino of a lysyl residue of the same or a different protein or peptide. Without wishing to be bound by theory, if such reactions were to occur involving the whey proteins present in the first dairy liquid, glutaminyl-lysyl side chain-side chain crosslinks would form between the protein components present, including crosslinks among and between the whey proteins (i.e,. intra- or inter-molecular cross linking). The modified dairy liquid produced by the action of the transglutaminase may include protein molecules crosslinked in this fashion. Generally, the treatment with transglutaminase is continued at a temperature between about 30° C. and about 60° C. for about 10 to about 300 minutes, and preferably for about 30 to about 100 minutes. After modifying the dairy liquid with transglutaminase, the transglutaminase may optionally be inactivated by, for example, a relatively brief exposure of the modified dairy liquid to an elevated temperature sufficient to achieve inactivation (i.e., optional heating step 2 in FIG. 1). The optional Inactivation step is not, however, required in order to practice this invention. The term "whey protein product" is employed herein to describe the product containing the modified whey proteins resulting from the action of transglutaminase on whey protein.

A significant further step in the present methods is the combination of the whey protein product from the transglutaminase treatment step (with or without inactivation in the optional heating step 2) and a second dairy liquid to form the dairy mixture. The second dairy liquid includes casein and is generally a milk liquid such as, for example, whole milk, reduced fat milk, or fat-free milk; preferably the second dairy liquid is not fortified with whey protein. The second dairy liquid may optionally be cultured with a milk-clotting or cheese-making culture prior to being mixed with the modified whey protein as indicated in FIG. 1. After mixing the second dairy liquid with the whey protein product, the resulting dairy mixture is clotted with a rennet. The rennet brings about coagulation of the dairy mixture to form a cheese curd and the corresponding whey liquid. As a consequence of having undergone modification by transglutaminase, a significant proportion of the starting whey protein from the first dairy liquid is retained in the cheese curd in the present method. The curd and newly formed whey resolve into separable phases which may be separated from each other by suitable conventional procedures such as centrifugation, filtration, application of pressure, or the like.

As the worker skilled in cheese making and dairy science appreciates, the protein contained in the first dairy liquid is transformed, according to the methods of the invention, by virtue of the treatment transglutaminase, and the optional treatment at an elevated temperature, as well as by the treatment with the rennet. Thus, although the starting first dairy liquid contains whey proteins whose properties and structures are well known to the skilled artisan, the products obtained by the sequential action of these enzymatic activities are not clearly understood. Therefore both the curd and the whey liquid may contain a large variety of protein and peptide components, as well as proteins of the starting dairy liquid that may not have been altered by the enzymatic activities applied in the process. For this reason, the terms "protein products originating from a dairy composition comprising casein and whey protein", "whey protein products", and equivalent phrases, are used herein to designate the products, heretofore uncharacterized, that may constitute the cheese curd and that may be present in the whey liquid. A substantial proportion of the original whey protein, present as whey protein products, is retained in the cheese curd of the invention rather than being found in the whey liquid. This result is heretofore uncharacterized in the field of cheese making and is therefore surprising to a worker of skill in the art.

The cheese curd retaining a substantial proportion of whey protein products may be processed further to make a large variety of cheese products, including, for example, soft, semi-soft, and/or hard cheeses. Such processing contributes factors of flavor, consistency, organoleptic properties, and the like, and is accomplished by processes such as fermentation with selected cheese-making microorganisms, subjecting the curd to additional enzymatic activities, and the like, in ways that are known to a person skilled in dairy science and cheese making.

The following examples are intended to illustrate the invention without limiting its scope. Unless otherwise indicated, percentages are by weight.

EXAMPLE 1

Preparation of Cheese Curds Containing Whey Protein Products.

A 32% solution of whey protein (N70, Meggle, Munich, Germany) was prepared. Aliquots (6.25 g) of this solution were transferred to a series of containers in order to prepare various samples of this experiment. Varying amounts of a transglutaminase preparation (Novo Nordisk, PPQ 6117, Franklinton, N.C.) containing 0.71 units/mL (where 1 unit is defined as the amount of enzyme that catalyzes the formation of 1.0 micromol hydroxamate per minute under the conditions of the assay (Folk, J. E. et al., *J. Biol. Chem.* 240:2951 (1965)), and mixed with sufficient of water to provide a total volume of 1.2 mL, was added to the samples. The containers were then incubated at 55° C. for 90 min to obtain whey protein products.

The second dairy liquid was skim milk (40 mL with a pH of about 6.7) which was supplemented with 62 μL of a 1:25 dilution of Cal-Sol™(45% $CaCl_2$ from Chr. Hansen, Milwaukee, Wis.), and with 0.12 g glucono-delta-lactone. The second dairy liquid was pre-incubated at 31° C. for 50 minutes. About 20 mL of the conditioned skim milk were then added to a whey protein product sample and homogenized for 10 seconds to form the dairy mixture. The remaining 20 mL of the supplemented skim milk, further supplemented with 6.0 μL of rennet solution (Chr. Hansen, Milwaukee, Wis.) containing 555 International Milk Clotting Units (IMCU) of activity/mL (1 IMCU is defined as the amount of enzyme required to clot 10 mL of reconstructed skim milk in 100s at 32° C.), was then added to the dairy mixture. The samples were then incubated at 31° C. for 30 minutes.

Two controls were used. Control 1 was a conventional cheddar cheese process; this control represents the normal whey and curd production without using transglutaminase; thus, control 1 curd would not contain significant amounts of whey protein. Control 2 comprised 7.45 g of whey protein solution containing 1.4 g of whey protein, and 40.4 g recovered whey containing 0.3 g of whey protein which was from the same conventional cheddar process as used in control 1; this control did not contain significant amounts of casein. The resulting curd samples were cut in situ, and heated from 31 to 39 ° C. over about 30 minutes. In order to measure the content of whey protein products in the curd, the curded preparation was centrifuged at 1,500 rpm for 10 min at 25° C., the whey was decanted and both whey and curd weighed. The protein content of the whey was determined using Lowry protein assay. The whey protein product retained in the curd was obtained by difference from control 2. The total curd solid was determined by drying the wet curd in a microwave oven. The increase in total curd solids was determined relative to control 1. The results (based on triplicate samples) are presented in Table 1.

TABLE 1

Effect of transglutaminase activity on incorporation of whey protein product into cheese curd

| Sample | Trans-glutaminase (mL) | Wet Curd (g) | Protein in Whey (%) | Calculated Protein in Curd (g) | Total Curd Solid (g) | Increase in Curd Solid (%) |
|---|---|---|---|---|---|---|
| Control 1 | 0.0 | 5.4 | 0.8 | 0.97 | 1.7 | 0 |
| Control 2 | 0.0 | 5.3 | 4.3 | 0.98 | 0 | — |
| 3 | 0.2 | 12.8 | 3.7 | 0.95 | 2.7 | 59 |
| 4 | 0.4 | 13.6 | 3.4 | 1.09 | 2.8 | 65 |
| 5 | 0.8 | 13.9 | 3.4 | 1.10 | 3.0 | 76 |
| 6 | 1.2 | 15.4 | 3.0 | 1.29 | 3.1 | 82 |

Control 1 provides the normal or conventional amount of protein product obtained using a conventional cheddaring process. Control 2 provides the results obtained in the absence of transglutaminase; control 2 does have essentially the same amount of whey protein as the original samples 3–6. Inventive samples 3–6 in Table 1 show less protein remaining in the whey and more retained in the curd as the amount of transglutaminase used increased. Moreover, increased amount of total curd is obtained as the amount of transglutaminase used increased.

These experiments demonstrate that the whey protein product obtained after whey protein is treated with a transglutaminase is retained to a significant extent when combined with skim milk and then curded with rennet. The fact that this curd is obtained by the successive application of transglutaminase to whey protein and mixing the product with milk to provide a curd using rennet contrasts sharply with the much lower yield of curd solids in the cheddar control number 1 and with the absence of curd formation found in the whey control number 2. Therefore the production of cheese curd by the inventive process, containing enhanced amounts of whey protein product, is unknown in the art of cheese making and dairy science.

EXAMPLE 2
Effects of Increasing Whey Protein Content on the Incorporation of Whey Protein Products into Cheese Curd. A 32% solution of whey protein (N70 containing 70 percent protein; Meggle) was prepared. Various amounts of this solution were transferred to a series of containers in order to prepare the samples of this experiment. To the various containers, transglutaminase (Novo Nordisk, PPQ 6117, Franklinton, N.C.) and various amounts of water were added, as shown in Table 2 for Samples 2–5. The containers were then incubated at 50° C. for 90 min to obtain whey protein products.

Skim milk samples (40 mL) with a pH of about 6.7 were supplemented with 62 µL of a 1:25 dilution of Cal-Sol™ (45% $CaCl_2$ from Chr. Hansen, Milwaukee, Wis.), and with 0.12 g glucono-delta-lactone, and pre-incubated at 31 ° C. for 50 min. A portion (20 mL) of the pre-incubated skim milk were added to the whey protein product and homogenized for 10 s; the remaining 20 mL of the skim milk and 6.0 µL of rennet (Chr. Hansen, Milwuakee, Wis.) solution containing 555 IMCU/mL were added. The samples were further incubated at 31 ° C. for 30 minutes. Control sample 1 contained no whey protein or transglutaminase. The resulting curd samples were cut in situ and heated from 31 to 39° C. over 30 minutes. The resulting products were centrifuged, and analyzed for protein and for moisture as in Example 1. The results are presented in Table 2. (It is estimated that about 5–10% moisture is retained in the dried curd and contributes to the result in the last column of Table 2.)

TABLE 2

Effect of transglutaminase on incorporation of whey protein product into cheese curd.

| Sample | Whey protein (%) | Transglutaminase (Units) | Total dried curd (g) |
|---|---|---|---|
| 1 | — | 0 | 1.6 |
| 2 | 3.2 | 0.18 | 1.9 |
| 3 | 6.4 | 0.36 | 2.3 |
| 4 | 12.8 | 0.72 | 3.4 |
| 5 | 18.2 | 1.08 | 4.2 |

Control sample 1 in Table 2 establishes a control level of protein products in cheese curd based on a conventional cheddaring process. Inventive samples 2–5 of Table 2 demonstrate that the total solids content of dried curd increases in direct correlation with the increase in the amount of whey protein subjected to transglutaminase treatment. according to the method of the invention. In comparison with the control sample 1, the incorporation of whey protein into cheese curd using the present method is uncharacterized in the field of cheese making and dairy science, and is therefore an unexpected feature of the instantly claimed invention.

Figure 2:
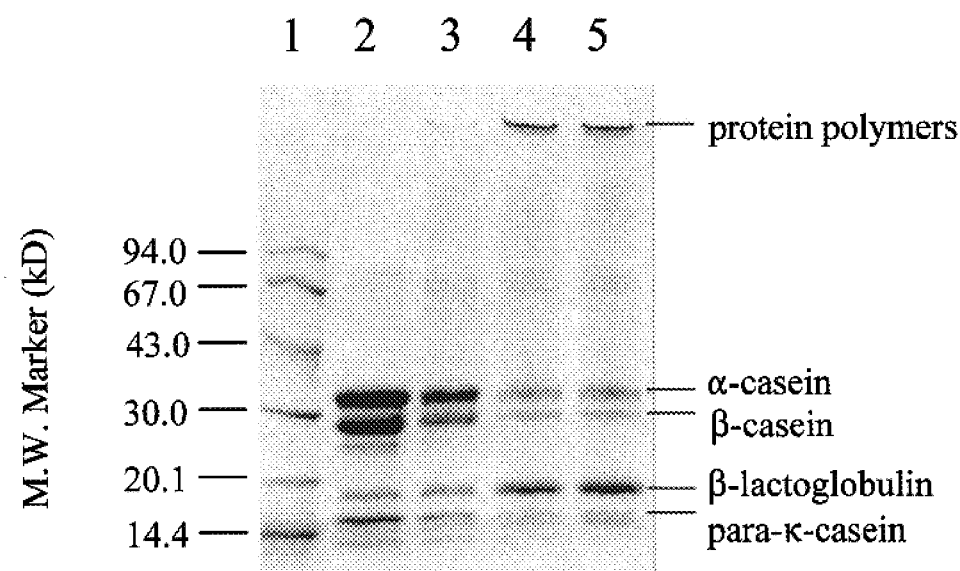
FIG. 2 is a SDS-PAGE 5–20% gradient gel of the curd solids obtained by treating various quantities of whey protein with transglutaminase. Lane 1: molecular weight markers. Lane 2: control (standard cheddar curd). Lanes 3, 4, and 5: inventive samples 2, 4, and 5, respectively, of Table 2 in Example 2.

Curd samples obtained from samples 1, 2, 4, and 5 were run on an SDS-PAGE 5–20% gradient gel, and are shown in Lanes 2–5, respectively, in FIG. 2. Lane 1 provides molecular weight markers. Lane 2 contains the standard cheddar curd of control sample 1. Lanes 3, 4, and 5 are from Samples 2, 4, and 5, respectively, of Table 2. The gel shows that the final cheese curd in the latter three samples contained significant amount of whey protein polymers that do not move far into gel (i.e., they essentially remaine at the sample well of the gel). This is especially pronounced for Samples 4 and 5 (Lanes 4 and 5, respectively). In addition, the relative quantity of casein was decreased significantly.

EXAMPLE 3
Scaleup of the Method of the Invention. Whey protein (2,270 g; WP 834, Alacen 834, New Zealand Milk Products, Wellington, New Zealand) was mixed with 7,718 g water and homogenized. The suspension was heated to 70° C. in a cooker, and cooled to 51 ° C. Transglutaminase (140 mL; Novo Nordisk, PPQ 6117, Franklinton, N.C.) was added and incubated for 60 minutes at 50 ° C. The mixture containing the whey protein product was then heated at 80° C. for 20 minutes, homogenized, and stored in the cold until used.

Milk (10 kg) was placed in a paddle tank of a cheese vat and heated to 31 ° C. During heating, 0.624 mL Cal-Sol™ (45% $CaCl_2$ from Chr. Hansen, Milwaukee, Wis.) was added. At 31 ° C., 1.31 g culture (CH-N22 frozen lactic culture, Mesophilic aromatic culture, type A, Chr. Hansen, Horsholm, Denmark) was added to the milk and incubated for 40–50 minutes. About 20% of the milk was removed from the tank and homogenized with 1125 g of the whey protein product prepared above; the homogenized mixture was then returned to the remaining milk culture in the paddle tank. Chymosin (1.10 mL, Chr. Hansen, Milwaukee, Wis.) solution containing 555 IMCU per mL was then added to the fermenting mixture, which was allowed to set at 31° C. for 30 minutes. The resulting curd was cut with vertical and horizontal cheese cutters throughout the tank. The temperature was then increased to 38–39° C. over a 30 minute time span. The curd was drained for about 1–2 hours and then pressed in a cheese presser for about 1 hr. The curd was then removed from the presser and mixed with 30 g salt; it was then replaced into the cheese presser and pressed overnight. The curd was cut, packaged under vacuum, and placed in an aging room. Curd from a standard cheddar process was used as a control.

The results from the pilot plant scale trials are shown in Table 3.

TABLE 3

Scaled Up Production of Cheese Curd

| Sample | Curd Obtained (g) |
| --- | --- |
| Cheddar control | 1073 |
| Inventive Method (3 runs) | 1500 ± 79 |

On a pilot scale, the treatment of whey protein with transglutaminase, and addition of the whey protein product to curded milk in the production of cheese, provides a significantly increased amount of curd relative to the control. Thus, the method of the invention is shown to be readily scaleable to pilot scale production.

We claim:

1. A process for making a cheese curd containing a substantial proportion of whey protein products and curded proteins originating from dairy liquids, wherein the process comprises the sequential steps of
   (i) providing a first dairy liquid fortified with whey protein:
   (ii) contacting the first dairy liquid with a transglutaminase to provide a modified dairy liquid containing whey protein products;
   (iii) blending the modified dairy liquid with a second dairy liquid containing casein to provide a dairy mixture;
   (iv) contacting the dairy mixture with a rennet to form cheese curd and whey liquid; and
   (v) obtaining the cheese curd by separating it from the whey liquid.

2. The process as described in claim 1, wherein the transglutaminase is isolated from a microbial source, a fungus, a mold, a plant, a fish, or a mammal.

3. The process as described in claim 2, wherein the transglutaminase is isolated from a microbial source.

4. The process as described in claim 3, wherein the transglutaminase is isolated from the genus Streptoverticillium.

5. The process as described in claim 1, wherein the first dairy liquid is heated to a temperature between about 55 and about 90° C. for about 2 minutes to about 40 minutes, and then cooled to a temperature of about 35 to about 60° C. prior to contacting the first dairy liquid with the transglutaminase.

6. The process as described in claim 1, wherein the modified dairy liquid is heated at a temperature of about 80 to about 95° C. for from about 5 to about 20 minutes and then cooled, prior to being blended with the second dairy liquid.

7. The process as described in claim 5, wherein the modified dairy liquid is heated at a temperature of about 80 to about 95° C. for from about 5 to about 20 minutes and then cooled, prior to being blended with the second dairy liquid.

8. The process as described in claim 1, wherein the second dairy liquid is cultured with a cheese-forming culture prior to being blended with the modified dairy liquid.

9. The process as described in claim 5, wherein the second dairy liquid is cultured with a cheese-forming culture prior to being blended with the modified dairy liquid.

10. The process as described in claim 7, wherein the second dairy liquid is cultured with a cheese-forming culture prior to being blended with the modified dairy liquid.

11. The process as described in claim 1, wherein the cheese curd is further treated to provide a soft, semi-soft, or hard cheese.

12. The process as described in claim 10, wherein the cheese curd is further treated to provide a soft, semi-soft, or hard cheese.

* * * * *

UNITED STATES PATENT AND TRADEMARK OFFICE
CERTIFICATE OF CORRECTION

PATENT NO.      : 6,224,914 B1
DATED           : May 1, 2001
INVENTOR(S)     : Xiao-Qing Han et al.

It is certified that error appears in the above-identified patent and that said Letters Patent is hereby corrected as shown below:

<u>Title page,</u>
Item [73], Assignee, replace "Norhtfield, IL" with -- Northfield, IL --.

This certificate supersedes Certificate of Correction issued January 29, 2002.

Signed and Sealed this

Tenth Day of December, 2002

JAMES E. ROGAN
*Director of the United States Patent and Trademark Office*